(12) United States Patent
Kampman

(10) Patent No.: US 6,461,313 B1
(45) Date of Patent: Oct. 8, 2002

(54) METHOD AND APPARATUS FOR MEASUREMENT OF SUBJECT'S SWAY

(76) Inventor: Ville Kampman, Kurjenpolvi 1 J 2, Fin-90580 Oulu (FI)

( * ) Notice: Subject to any disclaimer, the term of this patent is extended or adjusted under 35 U.S.C. 154(b) by 0 days.

(21) Appl. No.: 09/786,911

(22) PCT Filed: Sep. 9, 1999

(86) PCT No.: PCT/FI99/00727

§ 371 (c)(1),
(2), (4) Date: Jun. 11, 2001

(87) PCT Pub. No.: WO00/15111

PCT Pub. Date: Mar. 23, 2000

(30) Foreign Application Priority Data

Sep. 11, 1998 (FI) .................................................. 981947

(51) Int. Cl.$^7$ ............................................. A61B 5/103
(52) U.S. Cl. ....................................... 600/587; 600/595
(58) Field of Search ................................ 600/587, 595, 600/592, 594, 300

(56) References Cited

U.S. PATENT DOCUMENTS

| 2,670,729 A | | 3/1954 | Grant ............................ 128/2 |
| 4,830,024 A | * | 5/1989 | Nashner et al. .............. 600/559 |
| 5,146,929 A | | 9/1992 | Sawhill ........................ 128/781 |
| 5,337,757 A | * | 8/1994 | Jain et al. .................... 434/258 |

FOREIGN PATENT DOCUMENTS

| DE | 296 20 951 U1 | 3/1997 |
| WO | WO 91/15998 | 10/1991 |

* cited by examiner

Primary Examiner—Teresa Walberg
Assistant Examiner—Thor Campbell
(74) Attorney, Agent, or Firm—Connolly Bove Lodge & Bove LLP

(57) ABSTRACT

A method and apparatus for measuring the sway of a subject standing on a floor by transforming the motion of a stick capable of tilting in any direction coupled to the subject, wherein the motion of the body is transmitted to the stick, and the motion of the stick is detected. Motion of the stick is measured by an angle detector positioned close to its lower end.

8 Claims, 5 Drawing Sheets

8,21 cm²

METHOD AND APPARATUS FOR MEASUREMENT OF SUBJECT'S SWAY

Figure 1A:
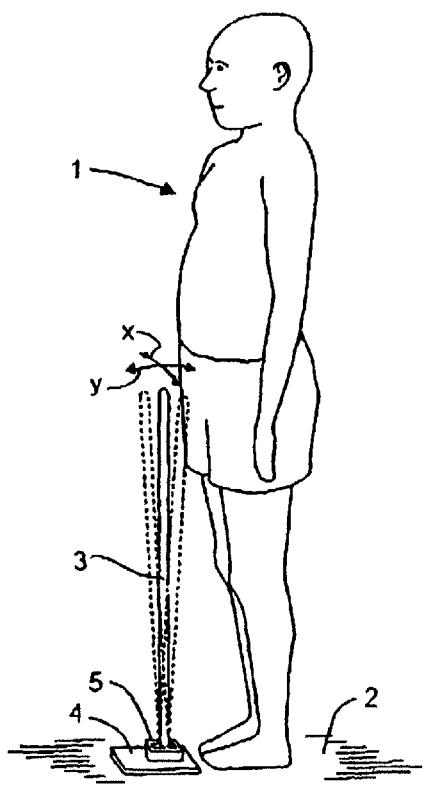

The invention is related to measurement of subject's sway by means of a method wherein a subject is placed to stand on a support surface for measurement of sway. The invention is related also to apparatus for measurement of subject's sway.

Within many fields of medicine it is necessary to clear up a patient's ability to keep one's balance. This may be concerned with various tests, e.g. aptitude or performance tests, or when studying the state of health of an elderly person. This kind of testing may also provide suggestions about a neurological or other disease having effects on the balance of a subject.

Various test methods and equipment have been developed by means of which the motions of the centre of gravity and balancing reactions may be measured indirectly. In some methods a subject is placed on a platform the tilting direction and force of which may be measured. In some other methods the pressure or force caused by the feet of a subject on different points of a platform is measured. A subject's ability to keep one's balance is tested also by evaluating the sway of the subject by means of so called Romberg test, for example. The sway is often evaluated by eye, only. Also such a solution is presented in which a pen is attached to a shaft, and at the other end thereof the shaft is attached to a subject's body whereby the pen draws a line on a paper describing the sway. However, the shaft must be quite long which causes that even small twisting motions of the body appear as large deviations in the description giving thus a distorted impression about the sway.

For the present, no such method or apparatus has been presented by means of which the sway itself could be measured. Measurements by means of the detectors attached directly to the body, for example, do not give good results because even small changes of the position of the joints, e.g. knees, change the position of the detector and cause vertical accelerations. As the accurate measurement of sway has not been possible, it has also been impossible to get information about the state of the health or performance of a subject by analyzing the sway. The object of tile invention is to provide a method and an apparatus for measurement of sway by which the foregoing problems may largely be solved.

To reach these objects the method according to the invention for measurement of sway is characterized by the features defined by claim 1. Further embodiments of the method of the invention are defined by claims 2 to 4.

The apparatus according to the invention for measurement of sway is characterized by the features defined by claim 5. Further embodiments of the apparatus of the invention are defined by claims 6 to 8.

The advantages of the method and apparatus of the invention include that the real sway motion in relation to a fixed supporting surface, e.g. floor, may be measured. Instantaneous or cumulative values of sway motion variables may be measured, and the sway motion may be registered in a memory and then be analyzed with various mathematical methods.

Figure 1B:
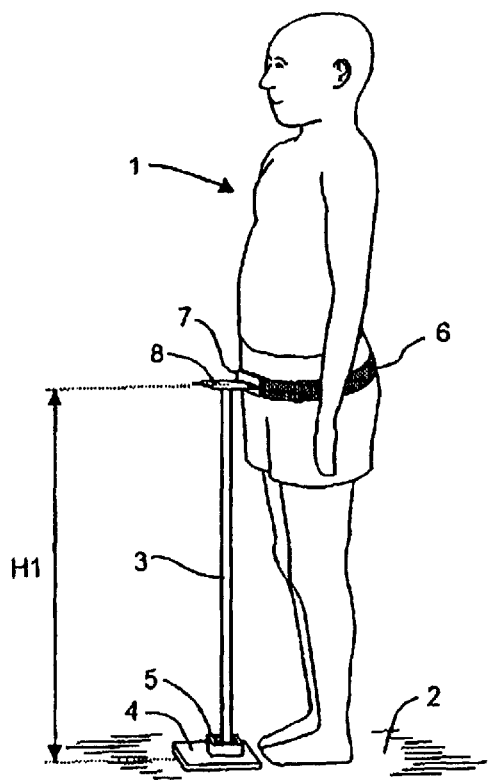
Figure 1C:
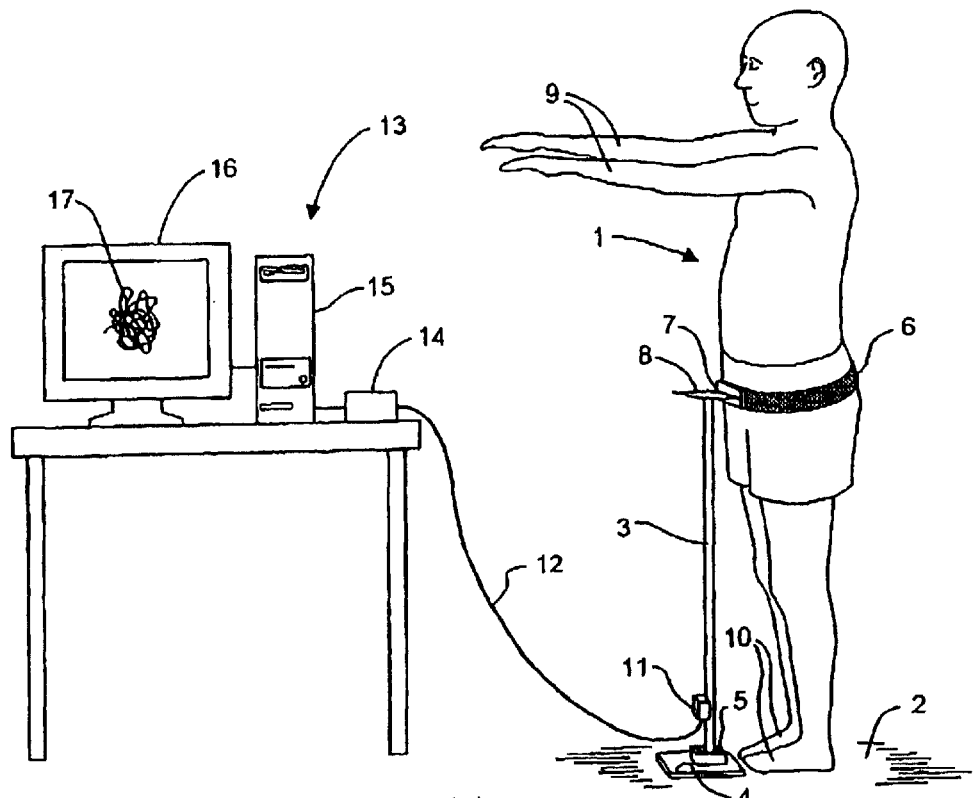
Figure 2:
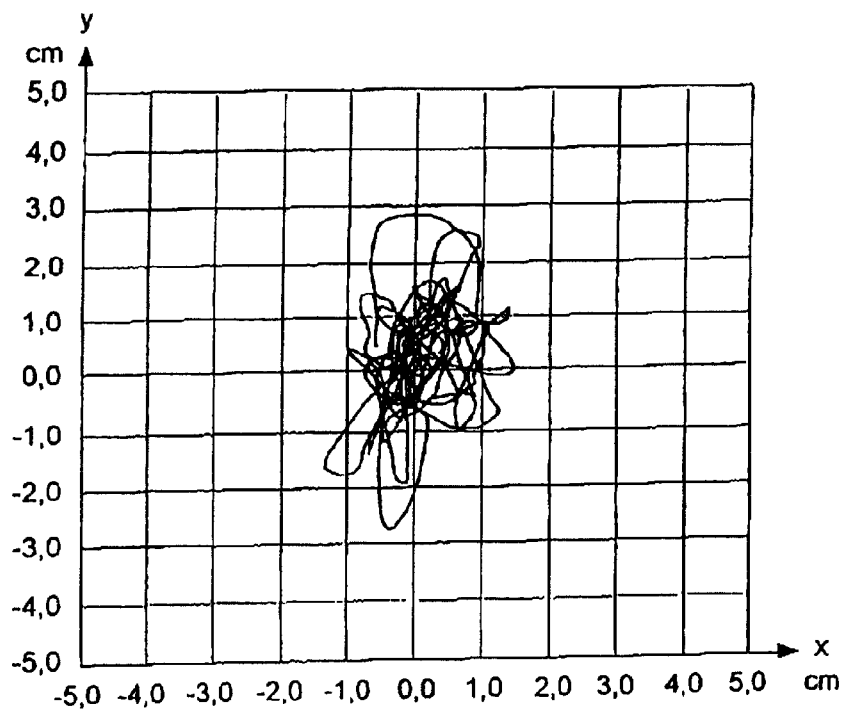
Figure 3:
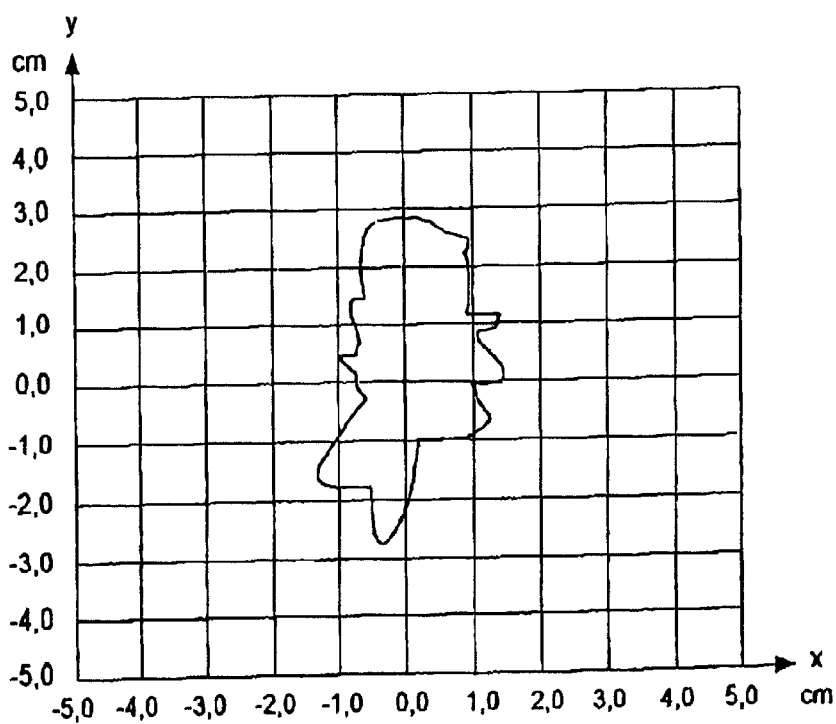
Figure 4:
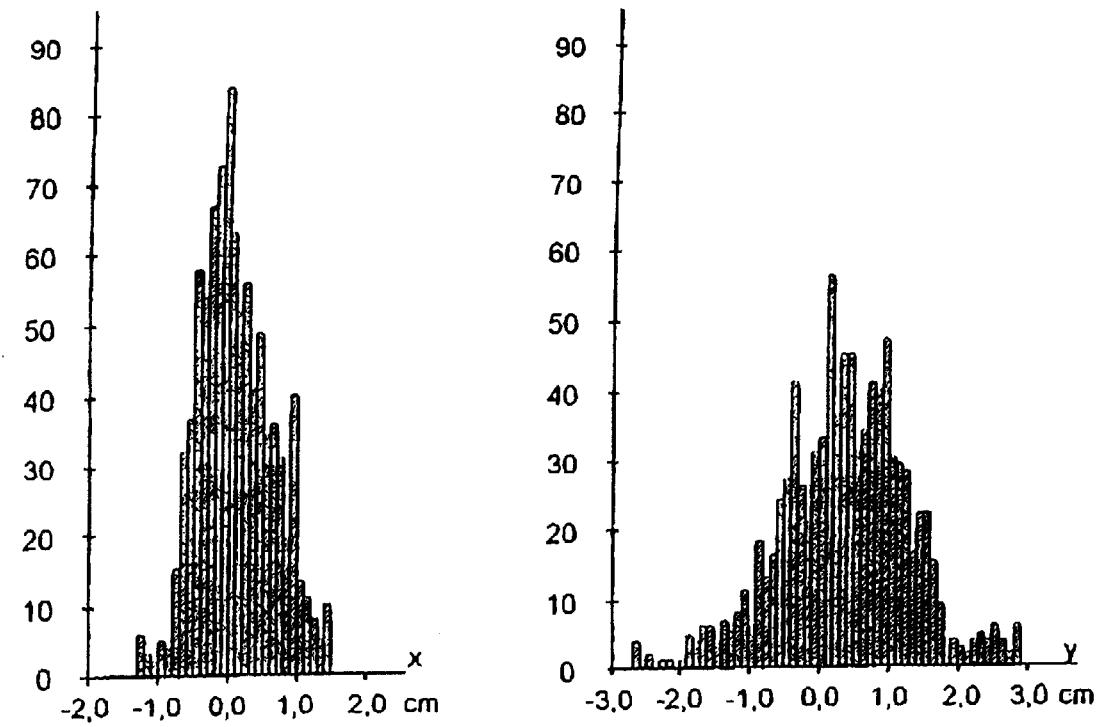
Figure 5:
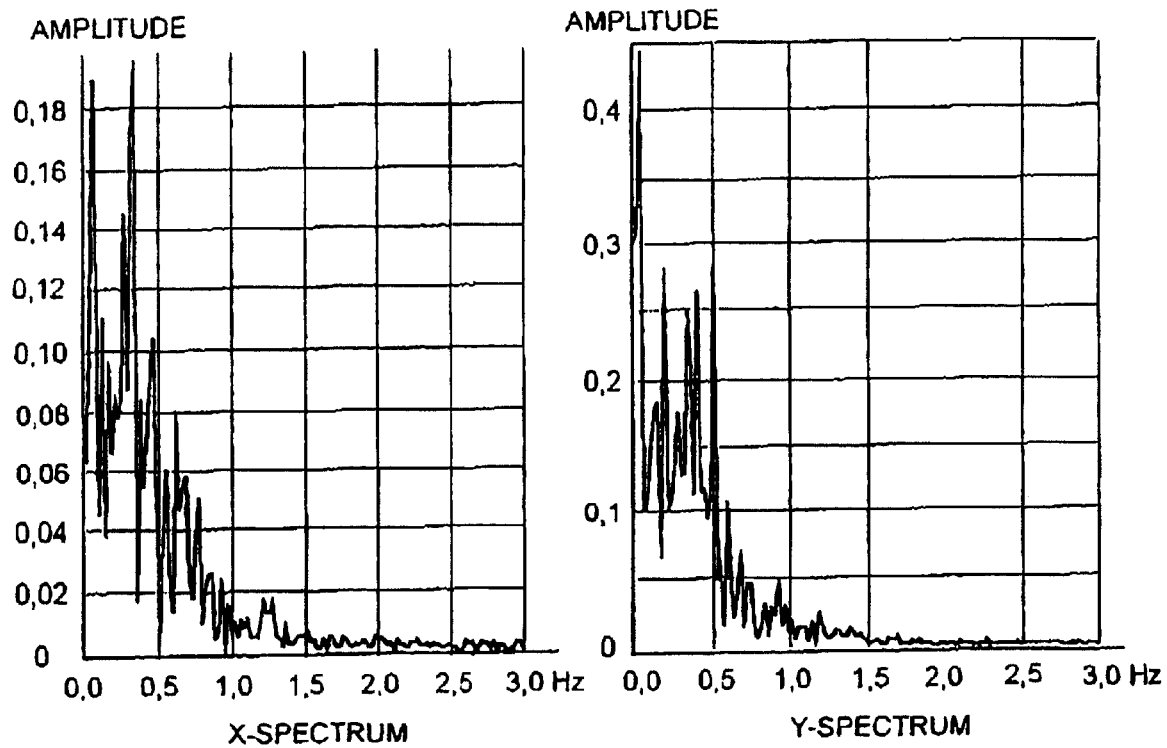
Figures 6, 7, 8:
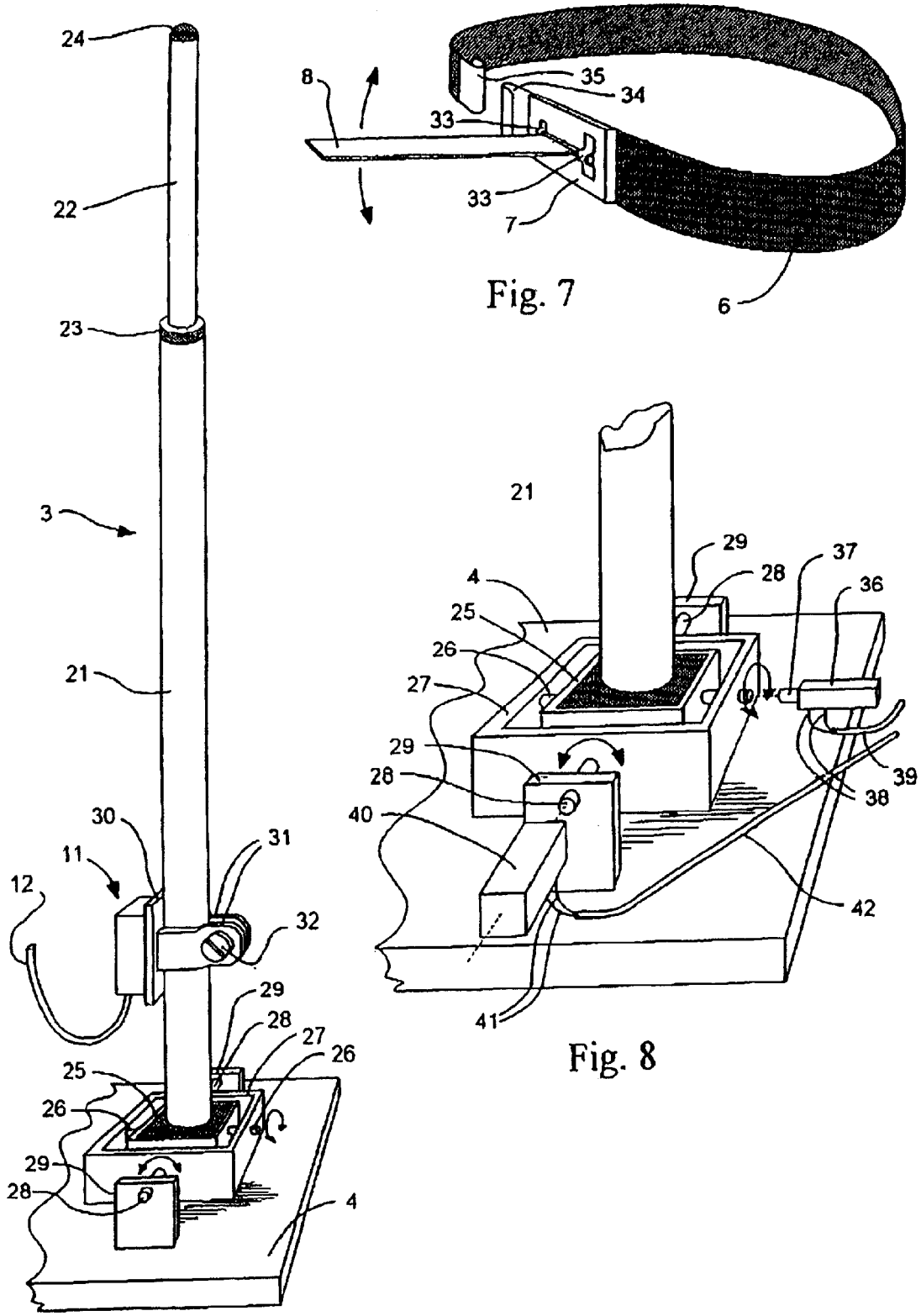
Figure 9:
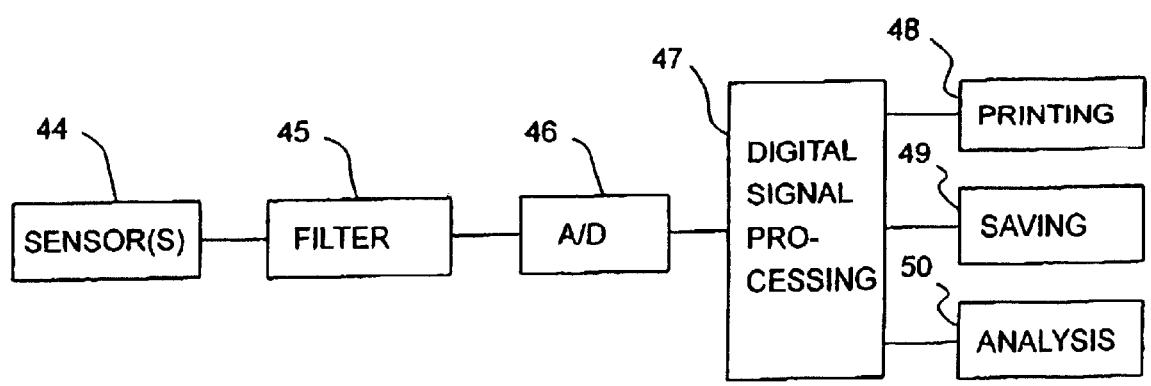

The invention and some embodiments thereof are described in more detail in the following with reference to the accompanying drawings wherein:

FIGS. 1(a), 1(b) and 1(c) illustrate as a schematic presentation an embodiment of the method and apparatus of the invention, FIG. 2 presents an example of a sway motion curve measured and registered by means of the method of the invention, FIG. 3 presents the approximated coverage of the sway motion curve of FIG. 2 and the calculated surface area thereof, FIG. 4 presents the histograms of the x- and y-deviations of the sway motion of FIG. 2, FIG. 5 presents the frequency analyses in x- and y-directions of the sway motion of FIG. 2, FIG. 6 presents schematically a possible realization of a stick and a detector attached thereto included in an embodiment of the apparatus of the invention, FIG. 7 presents schematically a possible realization of means for connecting the stick to the body of a subject under measurement included in an embodiment of the apparatus of the invention FIG. 8 presents schematically a possible realization of the detectors included in an embodiment of the apparatus of the invention, and FIG. 9 presents a block diagram of a possible realization of measuring and analyzing means included in an embodiment of the apparatus of the invention.

FIGS. 1(a), 1(b) and 1(c) illustrate the invention by presenting the method of the invention as a combination of three phases and respectively the measurement arrangement of the invention as a combination of three parts. In the invention it is essential that the sway motion of a subject 1 on a fixed support surface 2, e.g. floor, is transformed to the motion of a stick or equivalent 3 placed beside the subject (FIG. 1(a)). The stick is modelling rigid legs of the subject, and it should be made of suitable light and rigid material, e.g. plastic or aluminum. The stick 3 is coupled to the surface 2 on which the subject stands by an articulation structure 5 of two degrees of freedom so that it may tilt freely and with as small as possible friction to all directions, as is shown by arrows x and y in FIG. 1(a). Rotation of the stick 3 is advantageously prevented for making the measurement more simple and easy to carry out. For keeping the lower end of the stick 3 at its place during the measurement, the articulation structure 5 is attached to a support plate 4 which must be hold fast at its place on the support surface 2. This may be achieved by making the plate of a heavy enough material or by attaching the plate 4 to the support surface 2.

FIG. 1(b) illustrates the transformation of the sway motion of the subject 1 to the motion of the stick 3. Therefore, a belt 6 is attached around the subject's 1 body, the bell having a plate 7 to which a strip 8 is attached for transforming the sway motion of the body to the motion of the stick. The distance of the end of the stick 3 and the strip 8 from the supporting surface 2 is H1. The coupling between the subject's 1 body and the stick 3 must be such that it, on the one hand, transmits the sway motion of the body as well as possible and, on the other hand, allows tilting motions of the stick in accordance with swaying motions as well as possible. Obviously, the stick 3 must be as close to the body as possible but in such a way that there is no contact between it and the body. The coupling, e.g. a strip 8, must be as short as possible so that the twisting motions of the body have as small as possible effect on the motion of the stick. The coupling between the body and the stick is considered more closely later with reference to FIGS. 6 and 7.

In FIG. 1(c), means are added to the arrangement by which the motion of the stick 3 is measured. The subject 1 is in a certain position according to the measurement protocol. The measurement protocol is presented here in accordance with so called Romberg test in which the subject's feet 10 are side by side in contact with each other and directed forward and the arms 9 are extended horizontally forward with the palms being directed downwards. Subject's eyes are kept closed during the measurement. The belt 6 is placed low enough so that the breathing motions of the subject's diaphragm have as small as possible effect on the measurement results. A suitable attachment height of the belt is the level of the ridge of the subject's lilac bone.

In the example of FIG. 1(c) the motion of the stick 3 is measured by an angle detector 11 which is attached close to the lower end of the stick. In this way the effect of vertical accelerations on the measurement is minimized. Measurement equipment 13 includes an interface unit 14 and a microcomputer 15, 16 on the display of which a curve 17 is obtained which presents the motion of the stick 3 at a certain height.

FIGS. 6 and 7 present more closely a possible realization of the stick and the means for coupling the stick to the body of the subject. The length of the stick 3 may be adjusted steplessly. The lower part 21 and the upper part 22 are connected to each other with a telescopic joint, and the joint may be loosened for adjusting the length and tightened again with a conventional clamping ring 23. The joint of the lower end is formed by a swing arrangement in which a first swing piece 27 is attached pivotably with pins 28 to brackets 29 attached to the supporting plate 4. Another swing piece 25, on the other hand, is attached pivotably with pins 26 to the first swing piece 27. The pins 26 and 28 are located on the axes which are perpendicular to each other. The stick 3 is attached at its lower end 21 to the other swing piece 25. The angle detector 11 is attached to a plate 30 which is attached to the lower end 21 of the stick by means of a bracket 31 and a screw 32. A cable 12 is led from the detector 11 to the measurement equipment. A hemispherical magnet 24 is attached to the upper end of the stick 3.

FIG. 7 presents means by which the stick of FIG. 6 may be coupled to the body of the subject. A flexible belt 6 has at the ends thereof means 34, 35 for attaching the ends to each other. The length of the belt may be adjustable (not shown). A plate 7 is attached to the bell, and a metal strip 8 is attached to the plate 7 by a hinge arrangement 33. The hinge 33 is horizontal so that the metal strip 8 may pivot only up or down in the way indicated by arrows. The metal strip 8 suitable for magnetic attachement is set to attach to the magnet 24 at the end of the stick 3. This kind of attachment allows small changes of the angle between the strip 8 and the stick 3 without causing signifacant strains therein. As the stick is lightweight and the friction in the low end articulation arrangement is small, no sliding occurs in the magnetic attachment.

FIG. 8 presents schematically an alternative detector arrangement. The pivoting pins of the swing pieces 27 and 25, respectively, are connected (indicated by a broken line) to the corresponding axes 37 of potentiometers 40 and 36. Coductors 42 and 39 are led from connections 42 and 38, respectively, to the measurement equipment (not shown). The potentiometer 40 must be attached to the support plate 4 or a bracket 29 attached thereto, and the potentiometer 36 must be attached to the first swing piece 27 (attachements are not shown).

FIG. 9 is a block diagram presenting an exemplary realization of the measurement in greater detail. Analog signals from detector(s) 44 are filtered in block 45. Low pass filtering reduces disturbances and prevents folding of high frequencies. Next, analog-to-digital conversion is carried out in block 46. In block 47 the signals are processed digitally so that real-time printing on the screen (block 48) is obtained, the measurement results may be saved (block 49), and the results may be analyzed in the desired way (block 50), for example. In practice, the measurement arrangement may essentially consist of a microcomputer with a suitable measurement interface card, as is shown in FIG. 1(c).

Angle detectors or potentiometers provide analog signals indicating tilting angles in x- and y-directions. For making the measurement results more comparable, the angular deviations are advantageously converted to x- and y-deviations calculated for certain length of the stick, i.e. height from the support surface, which may be 80 cm, for example. For an angle detector the accuracy of which is ±0.01 degrees, the measurement accuracy of the sway deviation of the stick is then of the order of ±0.1 millimeters.

Taking into consideration the spectral analysis of the frequencies in x- and y-directions, the sampling frequency must be at least two times the highest frequency which is to be detected. A significant portion of the frequency spectrum is below 4 Hz. Then, the sampling frequency must be at least 8 Hz, and the sampling frequency of at least 20 Hz is preferred for assuring the detection of all important and essential features of the sway motion. Too low a sampling frequency may lead to erroneous results in the analysis of the sway motion.

A recommendable durance of the sway measurement is 30 to 60 seconds. In the measurements lasting over 60 seconds, the the subject easily loses the concentration.

The measurement results may be processed in the following way, for example. The measurement data converted to the sway deviations at a certain height are saved as x,y-value pairs in the memory of a computer and printed to an x-y-diagram at a rate of the sampling frequency. Despite the position of the stick in the beginning of the measurement, the first registered point may be taken as an assumed 0,0-point. As the measurement is finished, the motion data curve is relocated in regard to x-y-coordinates assuming that the sway motion occured around 0,0-point. For each point (x,y), the distance from and the instantaneous speed in regard to the preceding point may be calculated. By summing all the calculated distances the total length of the motion of the subject's body at a desired height is obtained. The total route length and the instantaneous speed may be printed before the conversion of the next pair of values. The measurement being finished, the average speed may be calculated by summing all the instantaneous speeds and dividing the result by the amount of the points. Also, the coverage of the motion data curve may be presented graphically and the area thereof may be calculated. Sway deviations in x- and y-directions may be analysed separately by means of histograms and by calculating standard deviations thereof, for example. Also, the frequencies of the sway motion may be analyzed.

FIGS. 2 to 5 present an example of the results of a measurement in accordance with the invention and the processing of the results. The exemplary measurement was carried out in the way illustrated by FIG. 1(c) for a multiple sclerosis patient. FIG. 2 presents the motion data curve, i.e. the route which the stick made at the height of 80 cm from the supporting surface during the measurement of 60 seconds. FIG. 3 presents an approximation of the coverage of the motion data curve as a graphical presentation and the calculated square area thereof which is 8.21 square centimeters. FIG. 4 presents histograms of the x- and y-deviations, i.e. the amounts of sample points classified according to the magnitude and direction of the deviation. The calculated standard deviations, in this case 0.53 cm in the x-direction and 0.93 cm in the y-direction, may be appended to the histograms. FIG. 5 presents the frequency analyses of the sway motion in x- and y-directions.

By means of the method and apparatus of the invention the sway motion may be measured and registered which is transmitted by a short coupling from the subject's body to a rigid stick. Accordingly, the sway motion of the stick follows very accurately the real sway motion of the body. Registered sway motion is easy to analyze. Naturally, there are many other analyzing possibilities than the foregoing ones. Measurement protocol may be made favourable for appearance of sway by applying the above mentioned protocol of Romberg test. The protocol and circumstances are also easily changed for analyzing the effect of the changes on the measurement results. The possibilities may be seen that in this way criteria or reference values may be achieved for indicating, on the one hand, what is normal sway and what may be characteristic for a certain disease or other abnormal state. By means of the invention it is also possible to achieve standards for measurement of sway by which comparable results may be obtained for subjects with widely varying physical properties.

It is possible, also, that sway is measured at the same time at different heights of the subject's body. This may be implemented by placing several sticks or equivalent beside the subject and coupling each one at different heights to the subject's body by means transmitting the sway motion. The motion of each stick is measured separately but simultaneously. In this way new information could be obtained about the qualities of the sway and the variations thereof caused by different reasons.

It is clear that the measurement arrangement according to the invention may be implemented in many other ways than what is described above. Instead of the stick a suitable piece of some other form may be used. For example, the motion of the stick or equivalent may be indicated in some other way than by means of an angle detector or a potentiometer. One possibility is to record the motion of the stick by two cameras. Also, the supporting and tilting arrangements and the realization of the coupling to the subject's body may vary widely.

The invention may be varied within the scope of the following claims.

What is claimed is:

1. Method for measurement of subject's sway in which method a subject (1) is set to stand on a support surface (2) for measurement, characterized in that therein:

a stick or equivalent (3) is set besides the subject (1) to be supported by the support surface (2) and to extend upwards therefrom so that it is capable of tilting freely to any direction (FIG. 1(*a*));

the stick or equivalent (3) is coupled at a distance (H1) from the support surface (2) to the body of the subject (1) for transmitting the motion of the body to the stick or equivalent (FIG. 1(*b*)); and the motion of the stick or equivalent (3) is detected (FIG. 1(*c*)).

2. Method of claim 1, characterized in that the detected motion of the stick or equivalent (3) is converted to digital data for further processing of the data and for analyzing and/or presenting the measurement results in a desired way (17; FIGS. 2 to 5).

3. Method of claim 1, characterized in that the stick or equivalent (3) is coupled to the body of the subject (1) at the height of the pelvis of the subject (1).

4. Method of claim 1, characterized in that the detected motion of the stick or equivalent (3) is converted calculatorily to the motion of the stick or equivalent at a certain standard height from the supporting surface.

5. Apparatus for measurement of subject's sway, characterized in that it includes:

a stick or equivalent (3), means (4,5) for supporting the stick or equivalent (3) on the support surface (2) to extend upwards therefrom so that the stick or equivalent (3) is capable of tilting freely to any direction (FIG. 1(*a*));

means (6, 7, 8) for coupling the stick or equivalent (3) at a distance from the support surface (2) to the body of the subject (1) standing besides the stick or equivalent; and means (11, 12, 13) for detecting the the motion of the stick or equivalent (3).

6. Apparatus of claim 5, characterized in that the means for supporting the stick or equivalent (21, 22) on the support surface and for making the tilting possible include an articulation structure of two degrees of freedom (25, 26, 27, 28, 29).

7. Apparatus of claim 5, charaeterized in that the means for detecting the the motion of the stick or equivalent (3; 21, 22) include a detector capable of measuring angle, like an angle detector or a potentiometer (36,40).

8. Apparatus of claim 5, characterized in that it includes means (13, 14, 15, 16; 46, 47, 48, 49, 50) for converting the detected motion of the stick or equivalent (3) to digital data and for further processing the data for analyzing and/or presenting the the data in a desired way (17; FIGS. 2 to 5).

* * * * *